United States Patent [19]

Di Schiena et al.

[11] 4,389,407
[45] Jun. 21, 1983

[54] 1,3-THIAZOLIDIN-4-YL-CARBOXYLIC ACID DERIVATIVES AND ANTIBACTERIAL COMPOSITIONS THEREOF

[75] Inventors: Michele Di Schiena; Vittoria Orrù, both of Trezzano sul Naviglio, Italy

[73] Assignee: Ausonia Farmaceutici s.r.l., Rome, Italy

[21] Appl. No.: 279,425

[22] Filed: Jul. 1, 1981

[30] Foreign Application Priority Data

Jul. 15, 1980 [IT] Italy ............................... 23455 A/80

[51] Int. Cl.³ .................... A61K 31/43; C07D 499/76
[52] U.S. Cl. ................................. 424/271; 260/239.1
[58] Field of Search ...................... 424/271; 260/239.1

[56] References Cited

U.S. PATENT DOCUMENTS

| | | | |
|---|---|---|---|
| 3,954,730 | 5/1976 | Metzger et al. | 260/239.1 |
| 3,971,776 | 7/1976 | Cimarusti et al. | 260/239.1 |
| 4,071,529 | 1/1978 | Christensen et al. | 260/239.1 X |
| 4,322,347 | 3/1982 | Cundall et al. | 260/239.1 |

Primary Examiner—Natalie Trousof
Assistant Examiner—Vera C. Clarke
Attorney, Agent, or Firm—Bucknam and Archer

[57] ABSTRACT

New derivatives of 1,3-thiazolidin-4-yl carboxylic acid of the general formula I

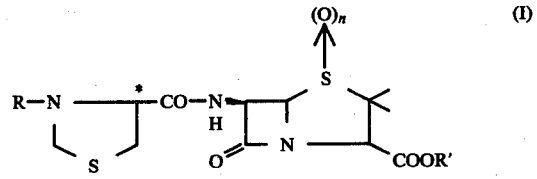

wherein:
R represents hydrogen, $(C_{1-4})$alkyl, aralkyl, phenyl, phenyl substituted by a halogen atom or a methoxy group, formyl, acyl, trimethylsilyl;
R' represents hydrogen, a pharmaceutically acceptable inorganic or organic cation, $(C_{1-4})$alkyl, 2,2,2-trichloroethyl, acetonyl, benzyl, benzyl substituted by nitro or methoxy, phenyl, nitrophenyl, benzhydryl or trimethylsilyl;
R' may also represent a radical capable of providing metabolic activation in vivo selected from acetoxymethyl, pivaloyloxymethyl, phthalidyl, benzoyloxymethyl, 5-indanyl, a group of formula

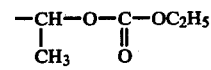

or a group of formula

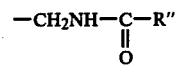

in which R" stands for $(C_{1-4})$alkyl, $(C_{5-6})$cycloalkyl or aryl; n may be zero or 1.

The compounds possess antibacterial utility against microbial infections in man, animals and plants.

11 Claims, No Drawings

1,3-THIAZOLIDIN-4-YL-CARBOXYLIC ACID DERIVATIVES AND ANTIBACTERIAL COMPOSITIONS THEREOF

DESCRIPTION OF THE INVENTION

The present invention refers to new 1,3-thiazolidin-4-yl-carboxylic acid derivatives of the general formula I

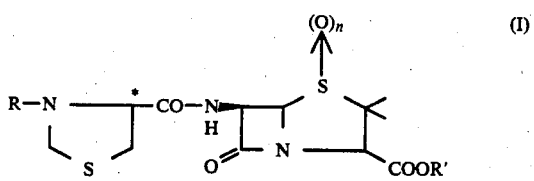

wherein:

R represents hydrogen, $(C_{1-4})$alkyl, aralkyl, phenyl, phenyl substituted by a halogen atom or a methoxy group, formyl, acyl, trimethylsilyl;

R' represents hydrogen, a pharmaceutically acceptable inorganic or organic cation, $(C_{1-4})$alkyl, 2,2,2-trichloroethyl, acetonyl, benzyl, benzyl substituted by nitro or methoxy, phenyl, nitrophenyl, benzhydryl or trimethylsilyl;

R' may also represent a radical capable of providing metabolic activation in vivo selected from acetoxymethyl, pivaloyloxymethyl, phthalidyl, benzoyloxymethyl, 5-indanyl, a group of formula

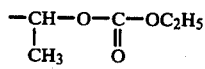

or a group of formula

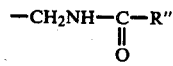

in which R" stands for $(C_{1-4})$alkyl, $(C_{5-6})$cycloalkyl or aryl; n may be zero or 1.

Characteristic meanings assumed by the radical R besides those already illustrated above are selected from methyl, ethyl, isopropyl, benzyl, trityl, acetyl, propionyl, trifluoroacetyl, benzoyl, benzoyl substituted by one to three hydroxy, methyl, methoxy, halo, amino and nitro groups, benzyloxycarbonyl, tert.-butoxycarbonyl or a radical deriving from a natural aminoacid.

Typical, but not limitative examples of the inorganic or organic cations represented by the radical R' are sodium, potassium, calcium and magnesium cations; cations deriving from organic bases such as, for instance, dibenzylamine, N,N-dibenzylethylenediamine, glucamine, N-methylglucamine, hexamethylenetetramine, 2-amino-2-hydroxymethyl-1,3-propanediol, arginine, lysine, proline, carnitine; or aluminum, zinc or silver cations.

Because of the presence of the asymmetric carbon atom at the 4-position of the thiazolidine ring, the compound of formula I may exist in one of the D- and L-configuration or as a racemic compound. Accordingly the invention contemplates all of these possibilities, though the L-configuration is the preferred one.

A further object of the invention is also represented by the salts of the compounds of formula I, in which the nitrogen atom of the thiazolidine nucleus has basic character, with pharmaceutically acceptable acids, e.g. citric, ascorbic, maleic, acetic, chloridric, nitric, hydrobromic and sulfuric acid.

Another object of the invention is represented by the pharmaceutical compositions for human or veterinary use, or pesticidal formulations for agricultural use containing as the active ingredient one or more of the compounds of formula I above or a pharmaceutically acceptable acid addition salt thereof.

It has been now surprisingly found that the compounds of formula I according to the invention are highly resistant to penicillinases when tested according to the method described by GROVE et al., Assay methods of antibiotics, A Laboratory Manual, Med. Encyclop. Inc., 1955, 7, or according to LORIAN V., Antibiotics and chemotherapeutic agents in clinical and laboratory practice, C. C. Thomas Publ., 1966, 242. They also have proven to be active against various pathogenic agents, e.g. gram-positive and gram-negative, aerobes and anaerobes bacteria, including β-lactamase producing strains.

More particularly, the compounds of formula I are active against gram-positive bacteria such as, for instance, *Staphylococcus aureus, Diplococcus pneumoniae, Streptococcus pyogenes, Streptococcus faecalis, Bacillus subtilis* and *Sarcina lutea*, as well as gram-negative bacteria such as, for instance, *Escherichia coli, Proteus mirabilis, Shigella sonnei, Klebsiella pneumoniae, Pseudomonas aeruginosa, Haemophilus influenzae* and *Salmonella typhimurium*.

The compounds of formula I according to the invention display also a remarkable activity against various pathogenic agents responsible of infections in vegetables, e.g.: *Pseudomonas syringae*, responsible of the bacteriosis of citrus-fruits and lilacs; *Pseudomonas phaseolicola* (halo blight of beans); *Pseudomonas aliicola* (bacterial mould of onions); *Pseudomonas savastandi* (scab of olive-trees); *Pseudomonas marginata* (scab of gladiolus); *Xantomonas phaseoli* (bacterial mildew of beans); *Pectobacterium carotovorum* (stump of potatoes and bacterial mould of iris rhizomes); *Erwinia amilovora* (necrosis of orchard branches); *Erwinia carotova* (bacterial mould of carrots); *Corynebacterium flaccum-faciens* (bacterial of beans); *Penicillum sp.* (bacterial mould of bulbs and corms).

As a representative, but not limitative example, it is reported in the following table the activity of the thiazolidin-carboxamido penicillanic acid sodium salt (compound of formula I wherein R=H; R'=Na; n=0) against two strains; this activity is expressed as minimum inhibitory concentration (M.I.C.).

TABLE 1

| Strain | M.I.C. (mcg/ml) |
|---|---|
| *Sarcina lutea* ATCC 9341 | 0.2 |
| *Escherichia coli* ATCC 10536 | 0.4 |

Accordingly, the new compounds which are one of the objects of the present invention may be administered to warm blooded animals, including humans, by oral, parenteral or topic route for combatting septicaemiae, meningitis, endocarditis; infections of the respiratory, gastroenteric and genitourinary tract and of the skin; ear-, nose-, throat infections; infections of bones; endoabdominal and endopleurical infections. They may also be employed in the asepsis of the skin before injections or urgical interventions; as well as in the disinfection of urgical tools.

The pharmaceutical dosage forms suitable for the ral administration may be, for instance, tablets, capules, pills, sugar coated tablets, syrups; suspensions, lrops, elixirs and granules. Pharmaceutical dosage orms suitable for the topical use are essentially represented by ointments, cremes, embrocations, collyria and otions.

All of the above mentioned pharmaceutical formulaions are prepared as known in the art and contain, ogether with the active ingredient, lubricant, diluent, xcipient, and sweetening agents as well as the commonly employed pharmaceutically acceptable additives.

In their quality of phytopharmaceuticals the compounds according to the invention can be employed in various administration forms, as an example aqueous olutions containing or not containing additional additives such as, for instance, talc or clay; powders, including the atomized preparations; sprays, both liquid and olids; suppositories, including the slow-release formulations; granules, including the slow-release formulaions; the forms absorbed on inert materials or ion-exchange resins; capsules and microincapsulated preparaions. All of these administration forms are well familiar o the art skilled technician.

Accordingly, the compounds of the present invention nay also usefully be employed for the preservation of ood-stuffs such as, for instance, citrus-fruits or potaoes; as, contrary to a lot of commonly employed substances, e.g. the bis-phenyl, they are effective antibiotic gents displaying a very low toxicity. The compounds f the invention can be prepared by different procelures. Thus, for instance, the amino group of a compound of formula II

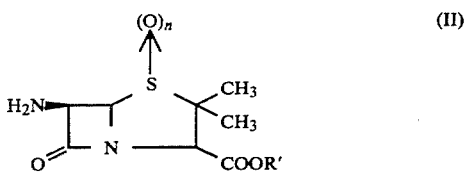

vherein R' is as above defined, is acylated with a suitble N-acylating reactant deriving from an acid of fornula III

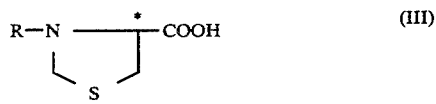

vherein R is as above defined. The protecting groups, if ny, must easily be removable under mild conditions. Typical example of a protecting group is the benzyloxcarbonyl radical. Such acylation reactions are well nown in the field of penicillins and cephalosporins see, for instance, Flynn, Cephalosporins and penicylins, Academic Press, 1972). Also the starting subtances of formula II and III are known to the art skilled echnician. The choice of the acylating agents will obviusly depend on the chemical nature of the substituents R and R', according to the common techniques and rinciples.

The N-acylating reactants deriving from the compound of formula III above are, for instance, the halides r those obtained through the reaction of III with the carbodiimide or the azide; preferably, an anhydride is employed and, advantageously, a mixed anhydride prepared in situ by reaction with ethyl- or isobutylchlorocarbonate, or pivaloyl chloride.

The choice of the reaction solvent and conditions, which essentially depend on the selected N-acylating agent, is a familiar task for the art expert. As an example, if the acylating agent is a mixed anhydride, the reaction may be carried out in an organic solvent selected from ethyl acetate, dimethylformamide, diethyl ether, tetrahydrofuran, dioxane, methylene chloride or analogous inert solvents; the temperature may be comprised between about $-40°$ C. and about the room temperature and, preferably, it is comprised between about $-20°$ and $-30°$ C.

A further advantageous methods for preparing the compounds of formula I comprises reacting the compounds of formula II and III above with silicon tetrachloride, according to Italian Patent Application No. 29445 A/77. The compounds of the invention can be isolated by means of techniques well known in the field of penicillins and cephalosporins such as, for instance, by crystallization, liophylization or spray-drying. A suitable isolating procedure comprising the absorption on chemically inert or activated material, as an example the ion exchanging resins; this procedure may be particularly useful when the obtained derivative must be used as food for animals or as phytopharmaceuticals.

The following examples are provided with the purpose of better illustrating the invention but in no way they must be construed as a limitation of the invention itself. The 6-amino-penicillanic acid will hereinbelow be indicated with the abbreviation 6-APA.

EXAMPLE 1

6-(1,3-Thiazolidine-4-yl)-carboxamido-penicillanic acid sodium salt (compound of formula I wherein R=H; R'=Na; n=zero)

13.3 Grams (0.01 mole) of 1,3-thiazolidine-4-yl-carboxylic acid were suspended in 250 ml of methylene chloride, keeping the temperature at $-15°$ C., then 12.0 g (0.1 mole) of pivaloyl chloride were slowly added in order to maintain the temperature below $-10°$ C. The mixture was left standing for 30 minutes, then it was cooled to $-20°$ C. and rapidly added with a solution of 31.7 g (0.1 mole) of the triethylamine salt of 6-APA in 500 ml of methylene chloride. During the addition, the temperature was kept at about $-10°$ C. After standing for 1 hour at $-10°$ C. and three hours without any external cooling, 1.0 g of coal and 2.0 g of Dicalite® were added, then the whole was filtered by a water-pump on a filter covered with Dicalite®. The limpid filtrate was evaporated under vacuum on a wather bath at 40° C. and the waxy, yellowish residue was twice washed by decantation with 50 ml of cyclohexane, then it was taken up with 200 ml of acetone and the resulting suspension was stirred for 2 hours. After eliminating the formed salts by filtration, the filtrate was added with a 1 M solution of 2-ethyl-hexanoic acid sodium salt in acetone and the resulting suspension was stirred for 3 hours. The formed precipitate was recovered by water-pump filtration, washed 3 times with 25 ml of acetone (3×25 ml) and dried in vacuo. 20.0 Grams of a white, water soluble product were obtained. TLC (thin layer chromatography) analysis of this product carried out by pouring on the same plate 6-APA and 1,3-thiazolidine- 4-yl-carboxylic acid as the reference compounds gave a unitary spot with an Rf value different from those of the reference compounds. To this purpose, 1% solutions in ph 7 0.1 M phosphate buffer of the final product and the reference compounds were prepared and 300 μl of each of these solutions were laid on a Silicagel F 254 plate (Merck); the eluting system was a 30/10/10 mixture (v/v) of n-butanol/acetic acid/water; the chromatograms were visualized with UV-light ($\lambda = 254$ nm) and ninhydrine.

EXAMPLE 2

6-(1,3-Thiazolidine-4-yl)-carboxamido-penicillanic acid phthalidyl ester (compound of formula I wherein R=H; R'=phthalidyl; n=0)

19.0 Grams of the compound of example 1 were suspended in 50 ml of anhydrous dimethylformamide cooled at 2° C. and the resulting suspension was added with 11.5 g of 3-bromophthalide dissolved in 20 ml of anhydrous dimethylformamide. The resulting mixture was kept at room temperature for 3 hours, the dimethylformamide was removed under vacuum at low temperature and the obtained residue was crystallized from isopropanolethyl acetate. The I.R. and N.M.R. analysis of the obtained precipitate are in agreement with the desired structure.

EXAMPLE 3

6-(1,3-Thiazolidine-4-yl)-carboxamido-penicillanic acid pivaloyloxymethyl ester (compound of formula I wherein R=H; R'=pivaloyloxymethyl; n=0)

88.4 Grams of the compound of example 1 were poured into 1 liter of acetone and the resulting mixture was first added with 41.5 of pivaloyloxymethyl chloride and then with 25 ml of an aqueous 25% solution of sodium iodide. After refluxing under stirring for 6 hours; the solvent was evaporated in vacuo, the obtained residue was washed three times by decantation with 100 ml of diethyl ether (3×100 ml) and finally dried at 50° C. in oven.

The I.R. and N.M.R. spectra are in agreement with the desired structure; TLC analysis [Silicagel F 254 plate (Merck); eluting system: cyclohexane/ethylacetate=1/1 (v/v); visualization: UV-light ($\lambda = 254$ nm) and iodine vapors] confirmed the substantial purity of the obtained compound.

EXAMPLE 4

6-[N-(2,2,2-Trichloroethoxycarbonyl)-L-1,3-thiazolidine-4-yl]-carboxamido-penicillanic acid 2,2,2-trichloroethylester (compound of formula I wherein R=Cl$_3$CCH$_2$—O—CO; R'=Cl$_3$C—CH$_2$—; n=0)

22.8 Millimoles of the compound of example 1 were suspended in 100 ml of acetone, which was previously dried on molecular sieves. To this suspension 48 millimoles of pyridine were added, the resulting suspension was stirred on an ice-bath in order to reach a reaction temperature of about 0° C., then the whole was added dropwise at 0° C. with 45.6 millimoles of 2,2,2-trichloroethyl-chlorocarbonate dissolved in 60 ml of acetone. After keeping overnight at 0° C., the reaction mixture was filtered from any insoluble, the precipitate was washed on the filter with acetone which was added to the mother liquors, the acetone solution was vigorously stirred and added with about 50 ml of water, whereby a solid began to crystallize. The water/acetone solution was further stirred for 3 hours until complete crystallization, then it was filtered, the obtained precipitate was washed with water and dried at temperatures lower than 40° C.

The I.R. and N.M.R. spectra are in agreement with the desired structure. The TLC analysis [eluting system: benzene/ethyl acetate=2/1 (v/v); visualization with iodine vapors] confirmed the substatial purity of the obtained compound.

EXAMPLE 5

6-[N-(2,2,2-Trichloroethoxycarbonyl)-L-1,3-thiazolidine-4-yl]-carboxamido-penicillanic acid 2,2,2-trichloroethyl ester, S-oxide (compound of formula I wherein R=Cl$_3$C—CH$_2$O—CO—; R'=Cl$_3$C—CH$_2$—; n=1)

Ten millimoles of the compound of example 4 were treated under stirring at 0° C. with 50 ml of chloroform and the resulting mixture was added dropwise with a solution of 11 millimoles of 85% 3-chloroperbenzoic acid in 25 ml of chloroform. The mixture was kept at 0° C. for 2 hours and was subsequently extracted with 50 ml of an aqueous 5% solution of sodium hydrogencarbonate and with 50 ml of water. The so treated chloroformic solution was dried over anhydrous sodium sulfate and finally evaporated to dryness in vacuo at a temperature lower than 40° C.

The I.R. and N.M.R. are in agreement with the desired structure. The TLC analysis [eluting system: benzene/ethyl acetate=2/1 (v/v); visualization with iodine vapors] confirmed the substantial purity of the obtained compound.

EXAMPLE 6

6-(N-Acetyl-1,3-thiazolidine-4-yl)-carboxamido penicillanic acid (compound of formula I wherein R=CH$_3$CO; R'=H; n=0)

4.0 Grams of N-acetyl-1,3-thiazolidine-4-yl-carboxylic acid were suspended in 25 ml of anhydrous acetone, the resulting suspensione was added under stirring with 2.3 g of triethylamine (TEA) and the mixture was cooled to −10° C. At this temperature, 2.75 g of pivaloyl chloride dispersed in 10 ml of anhydrous acetone were slowly added dropwise and, at the end of the addition, a drop of methylmorpholine was poured into the reaction flask. After 20 minutes, a previously prepared solution of 5.0 g of 6-APA in 5 ml of water and 10 ml of acetone was rapidly added together with 2.3 g of TEA, keeping the temperature at −10° C. The so obtained mixture was reacted for 2 hours allowing the temperature to raise to the ambient values, the formed solid was removed by filtration, washed on the filter with 20 ml of acetone and the limpid acetone solution was evaporated under vacuum at a temperature not higher than 40° C. An oily residue was collected, which was taken up with 100 ml of water, the aqueous phase was twice extracted with 40 ml (2×40 ml) of diethyl ether and the ether extracts were cast off. The aqueous phase was brought to pH 2 by means of aqueous 10% hydrochloric acid, than it was extracted three times with 50 ml (3×50 ml) of ethyl acetate. After drying the organic extracts over sodium sulfate and evaporating the solvent in vacuo at a temperature not higher than 40° C., 4.0 grams of a compound were obtained having the desired structure, as confirmed by the N.M.R. analysis carried out in CDCl$_3$ and using TMS as the internal standard:

δ=1.5 (s, 6H, CH3 gem.)
δ=2.05 (s, 3H, CH3—CO)
δ=3.15 (m, 2H, CH2—S)
δ=4.2 (s, 1H, CH—COOH)

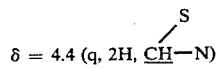
δ = 4.4 (q, 2H, CH—N)

δ=4.8 (m, 1H, CH—CO—NH)
δ=5.2 (m, 1H, CH—NH)
δ=7.2 (d, 1H, NH)
δ=8.0 (s, 1H, COOH)
=singlet; d=doublet; q=quartet; m=multiplet gem.-
=geminal.

EXAMPLE 7

-(N-pivaloyl-1,3-thiazolidin-4-yl)-carboxamidopenicillanic acid (compound of formula I wherein R=(CH3)3C—CO; R'=H; n=0)

10.0 Grams of N-pivaloyl-1,3-thiazolidine-4-yl-carboxylic acid were suspended in 50 ml of acetone, the resulting suspension was added with 4.56 g of TEA, keeping the temperature at −10° C. At the same temperature, a solution of 5.5 g of pivaloyl chloride in 25 ml of anhydrous acetone was slowly added. The reaction mixture was left standing for 20 minutes, then it was rapidly added with a previously prepared solution of 10.0 g of 6-APA in 10 ml of water and 20 ml of acetone and with 4.6 g of TEA, at a temperature of 0° C. After standing for 2 hours, allowing the temperature to raise from 0° C. to the ambient values, and standing two further hours at room temperature a solid formed, which was removed by filtration, washed on the filter with 20 ml of acetone and the limpid acetone solution was evaporated under vacuum at a temperature not higher than 40° C. An oily residue was collected, which was taken up with 100 ml of water, the aqueous phase was twice extracted with 50 ml (2×50 ml) of diethyl ether and said ether extracts were cast off. The aqueous phase, diluted with further 100 ml of water was brought to pH 2 by means of 10% aqueous hydrochloric acid and extracted three times with 50 ml (3×50 ml) of ethyl acetate. The organic phases was collected, dryed over sodium sulfate and evaporated at a temperature not higher that 40° C. The obtained residue was taken up with diisopropyl ether, by stirring until complete transformation of the gummy material into a solid crystalline substance which, after two hours, was filtered, washed with 20 ml of diisopropyl ether and dried in the air. Yield: 9.0 g. The TLC analysis [Silicagel plate F 254; eluting system: ethyl acetate/acetone/glacial acetic acid/water=5/2/1/1 (v/v); visualization: iodine vapors] gave a unitary spot with Rf=0.68.

The N.M.R. analysis in CDCl3, using TMS as the internal standard, was in agreement with the desired structure.

δ=1.3 (s, 9H, t-butyl)
δ=1.6 and 1.72 (s, 6H, CH3 gem.)
δ=3.2 (d, 2H, SCH2)
δ=4.3 (s, 1H, CH—COOH)

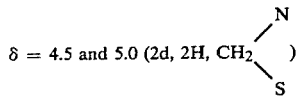
δ = 4.5 and 5.0 (2d, 2H, CH2)

δ=5.2 (t, 1H, CH—CONH)
δ=5.6 (m, 2H, CH—CH)
δ=6.3 (s, 1H, COOH)

δ=8.2 (d, 1H, NH)
s=singlet; d=doublet; t=triplet; m=multiplet
gem.=geminal

We claim:

1. A compound of formula

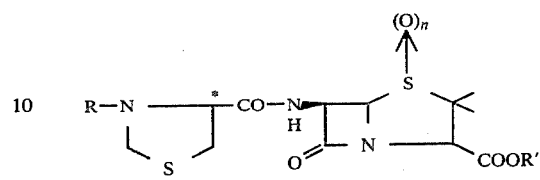

wherein:
R is hydrogen, trichloroethoxycarbonyl, acetyl or pivalyol;
R' represents hydrogen, a pharmaceutically acceptable sodium, phthalidyl, pivaloyloxymethyl or trichloroethyl,
n is zero or 1; the carbon atom of the 1,3-thiazolidine nucleus has the D- or L-configuration or the racemic form; or a salt thereof with a pharmaceutically acceptable acid.

2. A compound as defined in claim 1, wherein R and R' represent hydrogen and n is zero.

3. A compound as defined in claim 1, wherein R stands for hydrogen, R' for a sodium atom and n is zero.

4. A compound as defined in claim 1, wherein R stands for hydrogen, R' for phthalidyl and n is zero.

5. A compound as defined in claim 1, wherein R stands for hydrogen, R' for pivaloyloxymethyl and n is zero.

6. A compound as defined in claim 1, wherein R stands for 2,2,2-trichloroethoxycarbonyl, R' for trichloroethyl and n is zero.

7. A compound as defined in claim 1, wherein R stands for 2,2,2-trichloroethoxycarbonyl, R' for trichloroethyl and n is 1.

8. A compound as defined in claim 1, wherein R is acetyl, R' is hydrogen and n is zero.

9. A compound as defined in claim 1, wherein R is pivaloyl, R' is hydrogen and n is zero.

10. The compound according to claim 1 wherein said pharmaceutically acceptable acid is citric acid, ascorbic acid, maleic acid, acetic acid, hydrochloric acid, nitric acid, hydrobromic acid or sulfuric acid.

11. An antibacterial pharmaceutical composition for human, veterinary or agricultural use which contains a pharmaceutically acceptable carrier and as the active ingredient, an antibacterially effective amount of at least one compound of formula I:

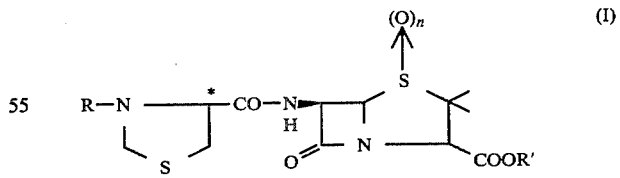

wherein:
R is hydrogen, trichloroethoxycarbonyl, acetyl or pivaloyl;
R' represents hydrogen, a pharmaceutically acceptable sodium, phthalidyl, pivaloyloxymethyl or trichloroethyl, n is zero or 1; the carbon atom of the 1,3-thiazolidine nucleus has the D- or L-configuration or the racemic form; and a salt thereof with a pharmaceutically acceptable acid.

* * * * *